(12) United States Patent
Allard et al.

(10) Patent No.: US 12,004,810 B2
(45) Date of Patent: Jun. 11, 2024

(54) METHOD AND SYSTEM FOR SELECTING A COLOR FILTER, OPTICAL ARTICLE COMPRISING SUCH A COLOR FILTER

(71) Applicant: ESSILOR INTERNATIONAL, Charenton-le-Pont (FR)

(72) Inventors: Rémy Allard, Champs sur Marne (FR); Daphné Silvestre, Paris (FR); Yannis Chenguiti, Aubervilliers (FR)

(73) Assignee: Essilor International, Charenton-le-pont (FR)

( * ) Notice: Subject to any disclaimer, the term of this patent is extended or adjusted under 35 U.S.C. 154(b) by 539 days.

(21) Appl. No.: 16/769,992

(22) PCT Filed: Dec. 6, 2018

(86) PCT No.: PCT/EP2018/083869
§ 371 (c)(1),
(2) Date: Jun. 4, 2020

(87) PCT Pub. No.: WO2019/110758
PCT Pub. Date: Jun. 13, 2019

(65) Prior Publication Data
US 2020/0383563 A1    Dec. 10, 2020

(30) Foreign Application Priority Data

Dec. 6, 2017 (EP) ..................... 17306709

(51) Int. Cl.
*A61B 3/06* (2006.01)
*G02C 7/10* (2006.01)
*G02C 7/02* (2006.01)

(52) U.S. Cl.
CPC .............. *A61B 3/066* (2013.01); *G02C 7/104* (2013.01); *G02C 7/024* (2013.01)

(58) Field of Classification Search
CPC ................................ A61B 3/066; A61B 3/022
(Continued)

(56) References Cited

U.S. PATENT DOCUMENTS 5,363,152 A * 11/1994 Reed, III ................. G02C 7/10
351/159.63
5,774,202 A * 6/1998 Abraham ................. G02C 7/00
351/219
(Continued)

FOREIGN PATENT DOCUMENTS

DE     2548395    5/1976
EP     1787579    5/2007
(Continued)

OTHER PUBLICATIONS

Ramamurthy, Vasudha & Narendran, Nadarajah & Freyssinier, Jean Paul & Raghavan, Ramesh & Boyce, Peter. (2004). Determining Contrast Sensitivity Functions for Monochromatic Light Emitted by High-Brightness LEDs. Proceedings of SPIE—The International Society for Optical Engineering (Year: 2004).*

(Continued)

*Primary Examiner* — Zachary W Wilkes
(74) *Attorney, Agent, or Firm* — Norton Rose Fulbright US LLP

(57) ABSTRACT

The invention relates to a method for selecting a color filter intended to be worn by a subject in order to improve his visual performance for a given visual task to be realized in a given environment. According to the invention, said method comprises the steps of: —submitting said subject to a colored spatio-temporal visual stimulus adapted to evaluate said visual performance for said given visual task, said stimulus being designed so that its chromaticity may be modified; —evaluating the visual performance of the subject based on his visual perception of said visual stimulus, the chromaticity of the visual stimulus taking at least two (Continued)

distinct values, each chromaticity being uniform; and —selecting said color filter based on the results of said evaluation. The invention further proposes an optical article comprising such a color filter. The invention finally provides a system for selecting a color filter using said method.

9 Claims, 2 Drawing Sheets

(58) Field of Classification Search
USPC .................................. 351/222–247, 159.66
See application file for complete search history.

(56) References Cited

U.S. PATENT DOCUMENTS

| | | | | |
|---|---|---|---|---|
| 6,755,529 | B2 * | 6/2004 | Stewart | A61B 3/06 |
| | | | | 351/243 |
| 7,641,344 | B2 * | 1/2010 | Artigas Verde | A61B 3/0091 |
| | | | | 351/239 |
| 2003/0223036 | A1 * | 12/2003 | Anderson | A61B 3/066 |
| | | | | 351/205 |
| 2012/0182520 | A1 | 7/2012 | Neitz et al. | |
| 2013/0176534 | A1 | 7/2013 | Frankfort et al. | |
| 2016/0242670 | A1 | 8/2016 | Suzuki et al. | |

FOREIGN PATENT DOCUMENTS

| | | |
|---|---|---|
| JP | H 3-4832 A | 1/1991 |
| WO | WO 2016/113506 | 7/2016 |
| WO | WO 2016/148984 | 9/2016 |
| WO | WO 2017/194898 | 11/2017 |
| WO | WO 2019/110758 | 6/2019 |

OTHER PUBLICATIONS

International Search Report and Written Opinion Issued in Corresponding PCT Patent Application No. PCT/EP2018/083869, dated Feb. 22, 2019.
Office Action issued in corresponding European Application No. 18814599.9, dated Mar. 27, 2023.
Rabin, J. et al., "Rapid Quantification of Color Vision: The Cone Contrast Test", *Investigative Ophthalmology & Visual Science*, 52(2), pp. 816-820, 2011.

\* cited by examiner

METHOD AND SYSTEM FOR SELECTING A COLOR FILTER, OPTICAL ARTICLE COMPRISING SUCH A COLOR FILTER

CROSS-REFERENCE TO RELATED APPLICATIONS

This application is a national phase application under 35 U.S.C. § 371 of International Application No. PCT/IB2018/083869 filed 6 Dec. 2018, which claims priority to European Patent Application No. 17306709.1 filed 6 Dec. 2017. The entire contents of each of the above-referenced disclosures is specifically incorporated by reference herein without disclaimer.

TECHNICAL FIELD OF THE INVENTION

The invention pertains to the domain of optometry and to the selection of a chromatic filter according to the wearer's sensitivity.

More precisely, the invention relates to a method for selecting a color filter intended to be worn by a subject in order to improve his/her visual performance for a given visual task to be realized in a given environment.

The invention also proposes an optical article comprising a color filter chosen using such a selection method.

Another object of the invention is to provide a system for selecting a color filter using said selection method.

BACKGROUND INFORMATION AND PRIOR ART

It is well known in the art of ophthalmic filters that color, also known as "chromatic", filters can improve, or degrade, the visual sensitivity of a wearer of this color filter, depending on the environment conditions (luminance levels, spectral content of surrounding lighting, spatial and/or temporal frequencies), visual task (reading, driving, . . . ) and observer's factors (e.g. age, ethnicity, pathologies, . . . ).

Usually, the color of a filter is chosen subjectively by the wearer among many possible color filters according to wearer's qualitative judgment or belief: preferred perception, aesthetic consideration, belief in enhanced vision (e.g. orange for fog and brown for sunny days).

However, the correlation between qualitative preference and visual performance is low.

Therefore, the true needs of the wearer for a given visual task is often not (or little) considered to optimize his/her visual performance for this task in a given environment. In other words, there is no objective quantification of visual performance to select optimal color filter.

SUMMARY OF THE INVENTION

Therefore one object of the invention is to provide a solution for optimizing the spectrum prescription in order to select the optimal color filter for specific visual functions and conditions.

A further object of the invention is to provide a color filter selection method which can reduce the subjective appreciation of color filters and to guide color filter prescription to optimize contrast sensitivity by choosing the best chromaticity for each wearer.

The above objects are achieved according to the invention by providing a method for selecting a color filter intended to be worn by a subject in order to improve his/her visual performance for a given visual task to be realized in a given environment, said method comprising the steps of:
  submitting said subject to a colored spatio-temporal visual stimulus adapted to evaluate said visual performance for said given visual task, said stimulus being designed so that its chromaticity may be modified, the chromaticity of the visual stimulus taking at least two distinct values, each chromaticity being uniform;
  evaluating the visual performance of the subject based on his/her visual perception of said visual stimulus, the chromaticity of the visual stimulus taking at least two distinct values, each chromaticity being uniform; and
  selecting said color filter based on the results of said evaluation of the visual performance.

The above "chromaticity" of the visual stimulus is defined as a colorimetric quantity according to CIE 1931 color space (CIE stands for "Commission Internationale de l'Éclairage"): it basically represents the "color sensation" of the eye, i.e. the eye's response to a specific colored visual stimulus, i.e. a colored visual stimulus having a specific spectral density or spectral power distribution.

It should be stressed that two distinct colored visual stimuli, hence having different spectral densities, may cause the same response from the eye of the subject, that is the same color sensation. This phenomenon is called metamerism. It is understood by the term "metamerism", a perceived matching of the colors with different spectral power distributions.

Despite CIE standard, the perceived chromaticity of a visual stimulus is personal and depends on individual physiology of color perception. For instance, the actual spectral sensitivity of different retinal photoreceptors (short S, medium M or long L), or how information from these photoreceptors are combined in retina and brain. In the same manner, the chromaticity at which the visual performance is optimal varies from one person to another. This is why we assess visual skill for different uniform chromaticity to select the best chromatic filter.

In a preferred embodiment of the method, the visual stimulus is designed so that, while its global chromaticity is varied during the submission step, its spatial and temporal luminance profiles are unchanged.

Alternatively, the visual stimulus is designed so that its spatial and/or temporal luminance profile is varied while its chromaticity remains uniform.

The visual stimulus presented to the subject is preferably of the form $VS(\lambda,x,y,t)=C(\lambda)*L(x,y,t)$, where $C(\lambda)$ is the spectral density of the visual stimulus VS; and $L(x,y,t)$ represents the spatial and temporal luminance profiles of the visual stimulus VS.

Other advantageous and non limiting features of the method according to the invention are as follows:
  the selected color filter at the selection step optimizes the visual perception of said visual stimulus;
  the visual stimulus is designed to stimulate differently the M- and L-cones stimulation pathways of the eyes of the subject;
  the spatial and temporal luminance profiles of the visual stimulus are predetermined according to the subject's need for the given visual task;
  the selection method further comprises a comparison step consisting in comparing at least one of said visual performance evaluation results with a predetermined reference value, the selection of said color filter being further based on the result of this comparison;

at the selection step:
when the result of the comparison shows that the visual performance of the subject is improved, one chooses said color filter as having a spectral response $T_A$ so that the chromaticity of the environment surrounding the subject seen through said color filter is globally conform to said chromaticity during the corresponding submission step; and
when the result of the comparison shows that the visual performance of the subject is degraded, one chooses another color filter;
the color filter is chosen so that the L-/M-cones excitation ratio of the subject when he/she sees the given environment through said filter is substantially equal to his/her L-/M-cones excitation ratio when he/she is submitted to the relevant visual stimulus during the corresponding submission step;
the selection step further takes into account the spectral content of said given environment;
said spectral density $C(\lambda)$ of the visual stimulus is such as $C(\lambda)=w_1*C_1(\lambda)+w_2*C_2(\lambda)$, where $C_1(\lambda)$ and $C_2(\lambda)$ are different spectra designed to stimulate differently the L- or M-cones stimulation pathways of the eyes of the subject; and $w_1$ and $w_2$ are respective weights of said spectra;
the predetermined reference value is a value of visual performance previously evaluated using said selection method;
the evaluated visual performance is one of the following: spatial and/or temporal contrast sensitivity; visual acuity; chromatic sensitivity; spectral sensitivity; critical frequency fusion; and/or reading or driving ability.
said visual stimulus is generated by a color display;
at evaluation step, the visual performance is evaluated by using a test chart illuminated by ambient light source, the spectral density of said ambient light source being modified during the submission step.

The selection method according to the invention aims at maximizing the wearer's sensitivity for a given activity in a given environment. The various advantages of said selection method are:
prescribe a color filter personalized to the wearer's chromatic sensitivity. The chromaticity at which visual perception is optimal varies from one observer to another. Hence, the claimed selection method optimizes visual perception for a given observer;
prescribe a color filter personalized to the wearer's needs or activities (reading, navigation, driving, color vision). The spatial and temporal luminance profile can be adjusted to optimize vision according to the wearer's needs in order to optimize vision for specific tasks (e.g. low vs. high spatial and temporal frequencies, central vs. peripheral vision, low vs. high luminance intensity). Given a tradeoff between various visual functions, altering chromaticity can improve some visual functions and impair others. For instance, a given color filter could impair spatial acuity but improve temporal acuity, or vice versa.
prescribe a color filter personalized to the chromaticity of the environment of the wearer. Visual perception depends on the spectral content of the visual information entering the eye, which depends on the spectral density of the illumination, the spectral reflection of the environment and the chromatic filtering. Thus, the chromaticity of the environment in which the filter will be used can be taken into account to optimize visual perception. The selected filter can be adjusted for particular environments (e.g. when blue dominates, such as on the water, or when green dominates, such as in a forest).

A further object of the invention pertains to an optical article, e.g. an ophthalmic equipment for visual correction, comprising a color filter selected using a method of selection according to the invention.

Another object of the invention is to provide an inventive system for selecting a color filter intended to be worn by a subject in order to improve his/her visual performance for a given visual task to be realized in a given environment.

According to the invention, said system comprises:
display means configured to submit said subject to a colored spatio-temporal visual stimulus adapted to evaluate said visual performance for said given visual task, said stimulus being designed so that its chromaticity may be modified, the chromaticity of the visual stimulus taking at least two distinct values, each chromaticity being uniform;
evaluation means for evaluating the visual performance of the subject based on his/her visual perception of said visual stimulus displayed to the subject, the chromaticity of the visual stimulus taking at least two distinct values, each chromaticity being uniform;
selection means for selecting said color filter based on the results of said evaluation of the visual performance performed by the evaluation means.

DETAILED DESCRIPTION OF EXAMPLE(S)

The following description made with reference to the accompanying drawings given by way of non-limiting example makes it clearly understood what the invention consists in and how it can be reduced to practice.

Throughout the description, we will consider one or several subjects who are not colorblind people. Indeed, the invention is not dedicated to this kind of pathological people and cannot be implemented for this kind of people.

The selection method described here is designed to improve or optimize the visual performance of a subject (for the rest of the description, we will consider that the main subject is a man) for a given visual task to be realized in a given environment.

The evaluated visual performance of the subject is one of the following: spatial and/or temporal contrast sensitivity; visual acuity; chromatic sensitivity; spectral sensitivity; critical frequency fusion; and/or reading or driving ability.

The given environment relates to the lighting conditions surrounding the subject. It comprises all the visual contributions to the ambient luminance experienced by the subject under test.

The selection method according to the invention described hereafter allows revealing and measuring the spectral sensitivity of a subject wearing a color filter; in other words, the aim of the invention is to provide a color filter selection method which can reduce the subjective appreciation of color filters and to guide color filter prescription to optimize contrast sensitivity by choosing the best chromaticity for each wearer.

According to the invention, the method for selecting a color filter according to the invention comprises the steps of:
- submitting the subject to a colored spatio-temporal visual stimulus, hereinafter referred to as VS, in order to evaluate the visual performance (contrast sensitivity) for a given visual task (for example reading), the visual stimulus VS being designed so that its chromaticity may be modified;
- evaluating the visual performance of the subject based on his visual perception of said visual stimulus VS for at least two chromaticities of the visual stimulus (two "color sensations"), each chromaticity being uniform; and
- selecting said color filter based on the results of said evaluation of the visual performance.

The at least two chromaticities of the visual stimulus are two distinct values of the chromaticity at different moments of the visual stimulus used in the submission step.

By "uniform chromaticity", we mean that the visual stimulus, which has a certain (i.e. non zero) spatial extension in a plane in front of the subject and which comprises various zones of visual stimulation, causes the same visual color sensation whatever the zone of the visual stimulus, at a given moment during the visual stimulus.

Figure 1:
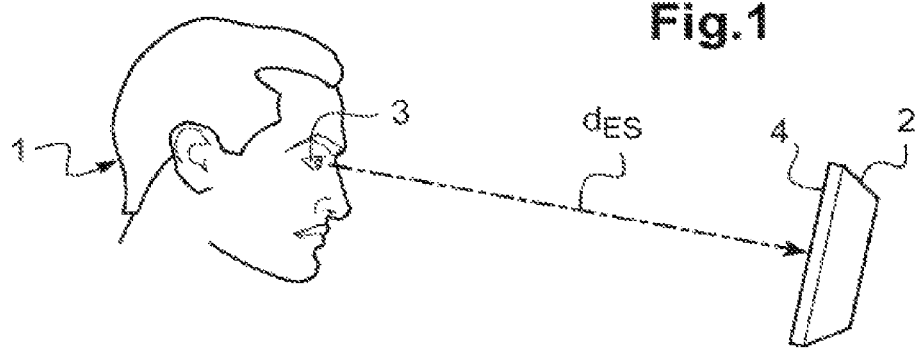
FIG. 1 is a schematic drawing showing a subject placed in front of a color display to test his contrast sensitivity and find the best color filter.

FIG. 1 represents a subject 1 (only his head is shown here) for which one wants to determine a color filter that can enhance his sensitivity to contrast, that is his capacity to distinguish between dark and light features, depending on their sizes and periodicities.

For this determination, the subject 1 is placed (standing or sitting on a chair) just in front of a color display 2 at a distance $d_{ES}$ between the eye 3 of the subject 1 and the screen 4 of the display 2.

For a contrast sensitivity test, the eye-screen distance $d_{ES}$ is comprised between 20 centimeters (cm) and 5 meters (m) to permit a sharp vision with visual compensation if needed. It is here set to a value of 100 cm. At this distance, only the near/intermediate vision is solicited.

Figure 2:
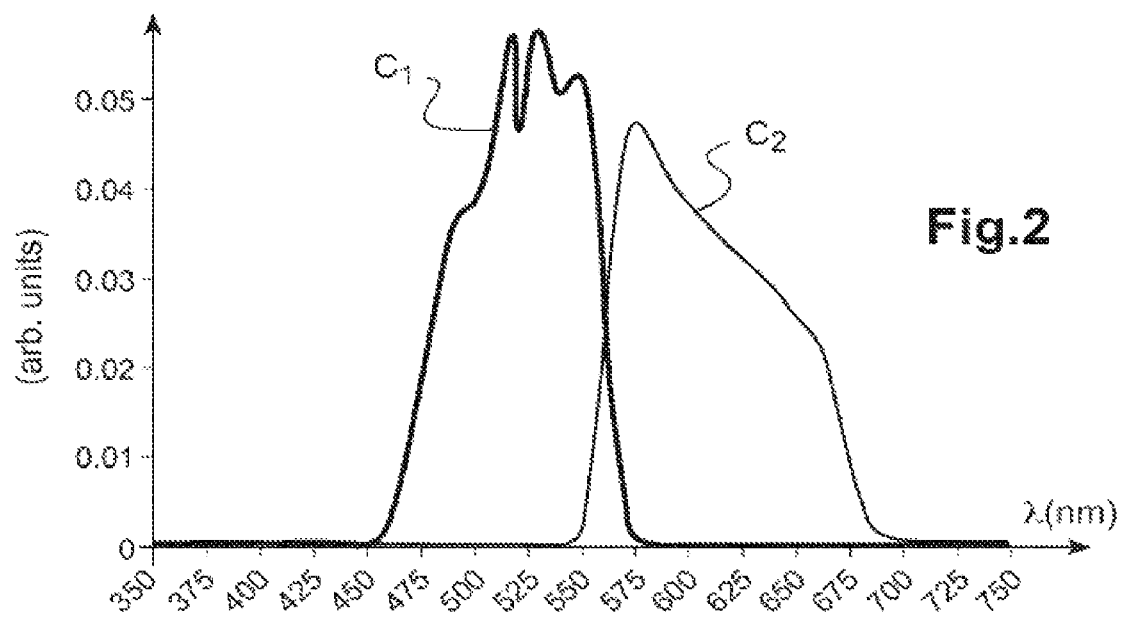
FIG. 2 is a graph showing the emission spectra curves of the two color guns of the color display of FIG. 1 used to produce a color visual stimulus.

The display 2 is a digital color display, where the screen 4 is a 3-colors screen having a two-dimensional array of "blue", "green" and "red" pixels. Here, for the contrast sensitivity test, only the green and red "color guns" are used to stimulate the vision of the subject 1. FIG. 2 represents two curves $C1(\lambda)$ and $C2(\lambda)$ which are respectively the spectra 5 of the green color gun of the display 2 and the spectra 6 of the red color gun of the display 2.

The color display 2 generates a visual stimulus VS visible to the subject 1 by displaying on the screen 4 different colored or black and white patterns, such as for example letters or numbers, meaning symbols, simple drawings, geometric figures, etc. . . .

In the present experiment, in order to test the contrast sensitivity of the subject 1, monochromatic sinusoidal gratings 7, 8 are displayed on the screen 4 for a predetermined time comprised between 10 milliseconds and 5 seconds.

Figure 3:
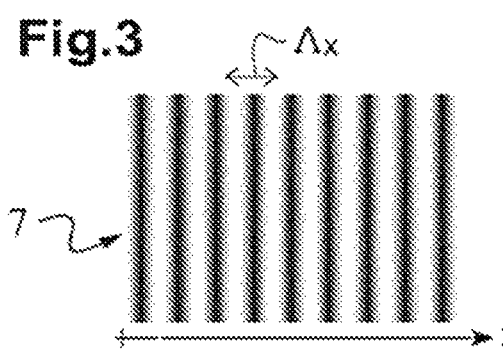
FIGS. 3 and 4 are schematic drawings of two sinusoidal gratings used to test the contrast sensitivity of the subject of FIG. 1.
Figure 4:
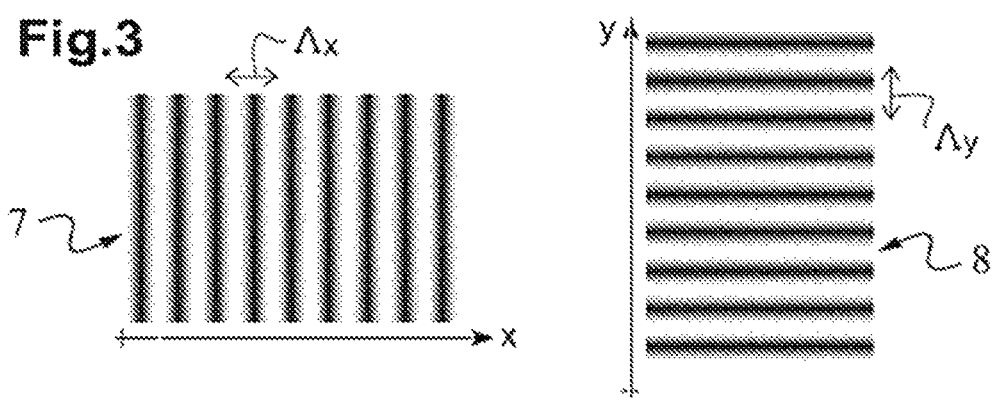

Here, the sinusoidal gratings 7, 8 are presented briefly for 500 ms, randomly oriented, either vertically (case of FIG. 3) or horizontally (case of FIG. 4).

The sinusoidal gratings 7, 8 are here "monochromatic", i.e. they present the same chromaticity on their whole surface. Indeed, by mixing in different proportions the two (green and red) color guns of the screen 4 (see FIG. 2), it is possible to generate a colored visual stimulus VS having a specific chromaticity, i.e. causing a particular "color sensation" to the subject 1 looking at the gratings 7,8 on the screen 4.

In the submission step, the subject is asked to look at the display screen 4 placed in front of him (see FIG. 1), and the subject's task is to discriminate the orientation (vertical or horizontal) of the displayed sinusoidal grating 7, 8.

Depending on the answer of the subject 1 about grating's orientation, the contrast of the sinusoidal gratings 7, 8 is varied: reduced following a correct answer and increased following an incorrect answer. In that way, it is possible to find the threshold contrast value at which the subject could perform the task relative to a criterion level (75% correct answer: mid-point between perfect performance, i.e. 100%, and chance, i.e. 50%).

In the preferred embodiment of the invention as illustrated in FIG. 1, the visual stimulus VS is such that its spatial and temporal luminance profiles are unchanged (i.e. same "light level sensation") while its global chromaticity is modified during the submission step.

The above property is realized with a visual stimulus VS presented to the subject which is of the form: $VS(\lambda,x,y,t)=C(\lambda)*L(x,y,t)$, where:
- $C(\lambda)$ is the spectral density (or "spectral content", or "spectrum") of the visual stimulus VS; and
- $L(x,y,t)$ represents the spatio-temporal luminance profile of the visual stimulus VS, i.e. a luminance-defined information/a luminance-based signal.

The contrast sensitivity CS can be defined as the inverse of the contrast threshold CT, that is, the smallest contrast c required to visually perceive a given signal $S(x,y,t)$, which represents a spatio-temporal pattern as a function of space $(x,y)$ and time $(t)$.

Thus, the spatial and temporal luminance profile $L(x,y,t)$ can be here defined as follows: $L(x,y,t)=L_0*[1+c*S(x,y,t)]$, wherein the signal $S(x,y,t)$ is such that $S(x,y,t)=\cos(2*\pi*\omega*t)*\cos(2*\pi*x/\wedge_x)*\cos(2*\pi*y/\wedge_y)$. The quantity $\omega$ is the temporal pulsation, $\omega$=500 ms; $\wedge_x$ and $\wedge_y$ are the periodicities (e.g. in millimeters) of the vertical and horizontal sinusoidal gratings 7, 8 (see FIGS. 3 and 4) respectively.

As specified above, the visual stimulus $VS(\lambda,x,y,t)$ is designed so that its spectral density $C(\lambda)$, and thus its chromaticity, can be varied to stimulate in different ways the eyes 3 of the subject 1.

By selecting spatial and temporal frequencies $k_x=2*\pi/\wedge_x$, $k_y=2*\pi/\wedge_y$ (see FIGS. 3 and 4), and $\omega$, which are relevant to the wearer's needs, the chromaticity at which the visual perception of these spatio-temporal frequencies by the subject 1 is optimized, could be found to optimize visual performance of the subject's needs.

To illustrate the technical solution, the current section provides a specific example of the perception of some luminance-defined information $L(x,y,t)$ that can be implemented.

In the current example, chromaticity $C(\lambda)$ can be adjusted to optimize contrast sensitivity at some specific spatio-temporal frequencies $k_x$, $k_y$, $\omega$ relevant to the subject's needs (e.g., optimize visual performance to low spatial frequencies and high temporal frequencies for navigation, sports or driving, and to high spatial frequencies and low temporal frequencies for manual detailed activities such as reading).

In other words, the present technical solution aims at determining the chromaticity $C(\lambda)$ at which the visual perception of the luminance-defined information, i.e. the spatio-temporal luminance profile $L(x,y,t)$, is optimized (improve sensitivity or enhance supra-luminal information thereby improving some visual performance).

The spatio-temporal luminance profiles $L(x,y,t)$ are determined according to the wearer's needs (e.g., low vs. high spatial and temporal frequencies, central vs. peripheral vision, mean luminance intensity).

The optimal perception of the luminance-defined information is found by evaluating (e.g., visual task or subjective judgments) the visual perception of the subject 1 in various chromaticities.

The effect of color filters on contrast sensitivity has been investigated in the scientific literature. But the contrast sensitivity facilitation with chromatic filters is still debated.

The present invention focused on a new paradigm taking into account a physiological approach based on short (S), medium (M), and long (L) cones (specific physiological sensors to process spectral sensitivity) distributions. For a given task and a given environment, the optimal color filters will be determined by optimizing the neural integration of cones, in particular the M- and L-cones The rationale behind the interaction between chromaticity and luminosity is that the luminance pathway of the visual system originates from the integration of the L- and M-cone pathways. However, S-cones play negligible role on luminance processing.

By varying the spectral density $C(\lambda)$ of the visual stimulus VS presented to the subject 1, the M-cones and L-cones can be stimulated in different proportions as the probability of a photon to be absorbed by a given photo-receptor (i.e. a S-, M-, or L-cone) depends on its wavelength $\lambda$ ($P_X(\lambda)$, X=S, M, or L).

Figure 5:
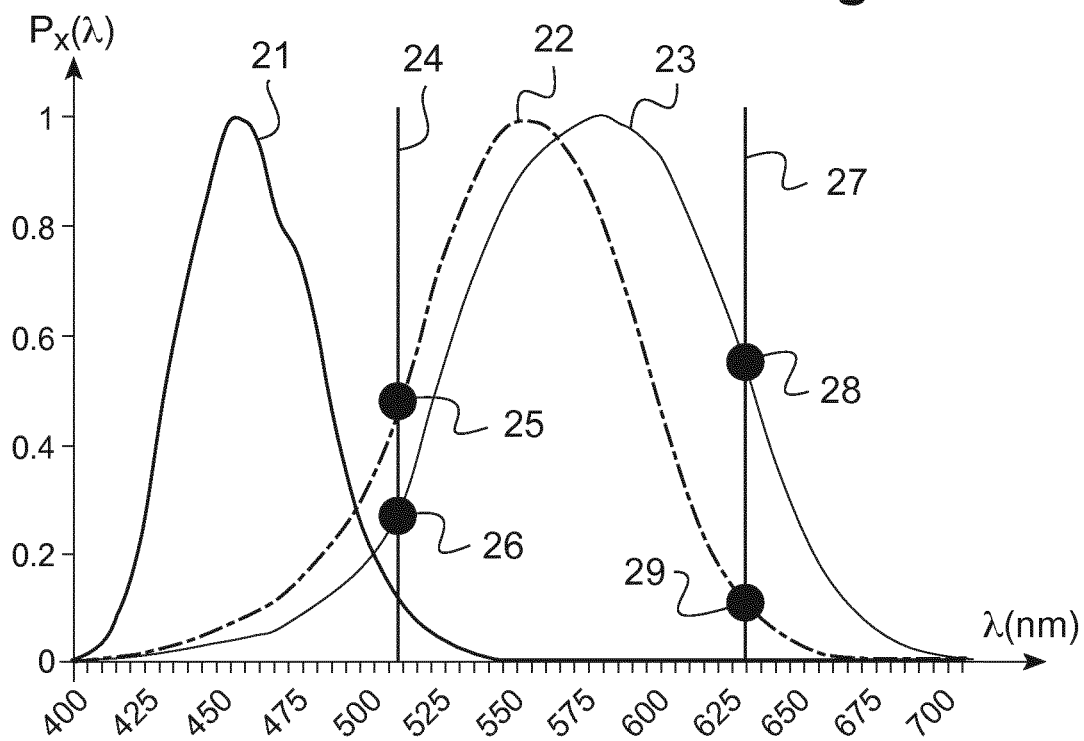
FIG. 5 is a graph showing the standard photon absorption probability curves for the S-, M-, and L-cones of the subject of FIG. 1, each curve being individually normalized by its maximum value.

FIG. 5 is a graph showing the standard (i.e. subject's independent) photon absorption probability $P_S(\lambda)$, $P_M(\lambda)$, $P_L(\lambda)$ curves 21, 22, 23 for the S-, M-, and L-cones respectively, each curve 21, 22, 23 being individually normalized (to 1) by its maximum value.

It can be understood from FIG. 5 that a visual stimulus at a single wavelength of 510 nm (see vertical line 24) will activate more the M-cones (point 25) than the L-cones (point 26) compared to a visual stimulus at a single wavelength of 630 nm (see vertical line 27 and points 28, 29).

One can calculate the activation $A_X$ of the X=S, M, L-cones as: $A_X = \text{integral}\{-\infty; +\infty; C(\lambda)*P_X(\lambda)\}$ and the L/M activation ratio $\alpha_{L/M}$ by $\alpha_{L/M} = A_L/A_M$.

Thus, given nonlinear integration of M- and L-cones pathways, some L- and M-cone activation ratio $\alpha_{L/M}$ can result in some contrast sensitivity gain within the luminance pathway of the visual system of the subject 1.

Ideally, the optimal activation ratio can be measured individually, but it could also be approximated for some groups (e.g., older subjects could tend to a different ratio compared to younger subjects).

Hence, in order to differentially stimulate the photoreceptors—M- and L-cones—responsible for the contrast sensitivity, the perceived chromaticity (depending on the spectral content $C(\lambda)$) of the visual stimulus VS is varied and takes at least two distinct values (two "color sensations").

For instance, this can be achieved with a spectral density $C(\lambda)$ which is preferably such as $C(\lambda)=w_1*C_1(\lambda)+w_2*C_2(\lambda)$, where $C_1(\lambda)$ and $C_2(\lambda)$ are the different spectra ("baseline chromaticities"; see FIG. 2) designed to stimulate differently the L- or M-cones stimulation pathways of the eyes 3 of the subject 1; and $w_1$ and $w_2$ are the respective weights of said spectra $C_1$, $C_2$.

In order to vary only the chromaticity and not the luminance (in cd/m$^2$) of the visual stimulus VS, the luminance of the baseline chromaticities $C_1(\lambda)$ and $C_2(\lambda)$ are equalized between each other, and the sum $w=w_1+w_2$ of the weights is kept substantially constant.

Within these constraints, modifying the respective weights $w_1$ and $w_2$ of the baseline chromaticities then varies the spectral content $C(\lambda)$ of the perceived visual stimulus VS, and hence the chromaticity (i.e. the "color sensation") of the visual stimulus VS, but without affecting the overall perceived luminance level (i.e. the "brightness sensation") of said visual stimulus VS.

The weights $w_1$ and $w_2$ at which the visual perception is optimized corresponds to the optimal cone activation ratio for the visual performance of the subject 1 in the given visual conditions.

Figure 6:
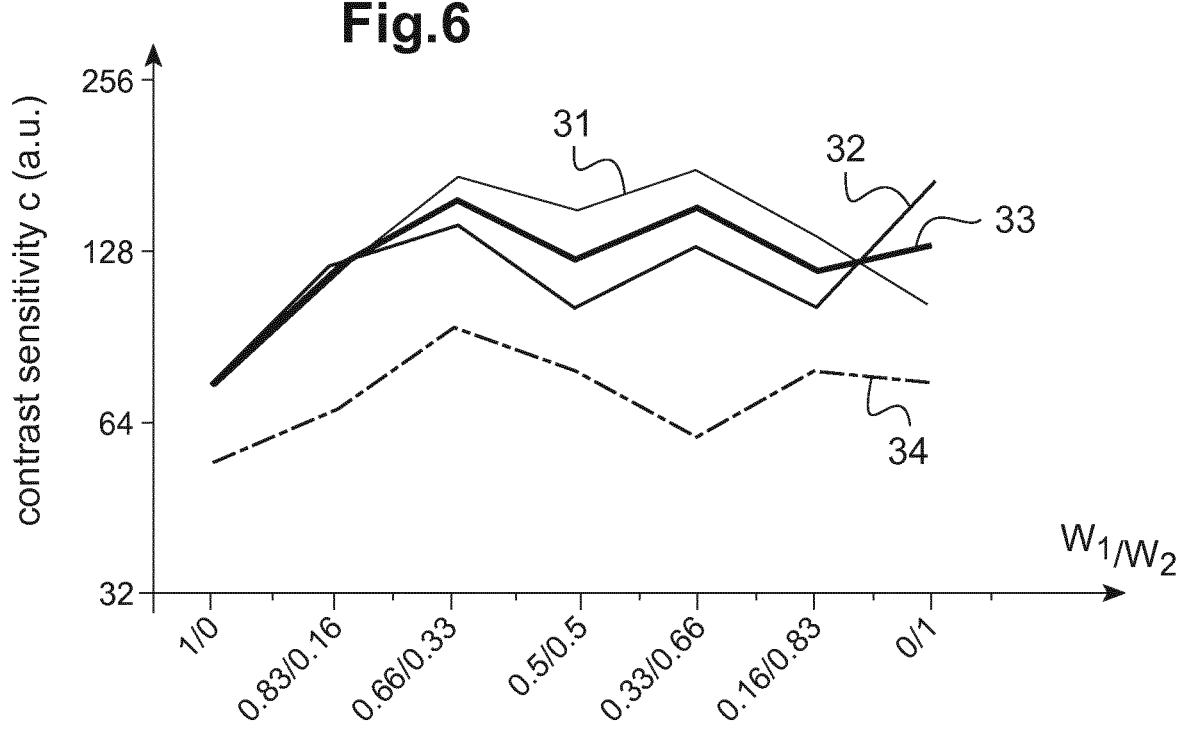
FIG. 6 is a graph showing the contrast sensitivity curves of four different subjects as a function of the relative weight of the two color guns of FIG. 2.

According to these principles, FIG. 6 shows the contrast sensitivity curves 31, 32, 33, 34 of four different subjects as a function of the relative weight $w_{1/2}=w_1/w_2$ of the two color guns $C1(\lambda)$, $C2(\lambda)$ of FIG. 2 (while $w_1+w_2$=constant).

As can be seen from FIG. 6, the contrast sensitivity c of the various subjects to the luminance sinusoidal gratings varies with respect to the chromaticity of the visual stimulus VS (as chromaticity is linked to the activation ratio $\alpha_{L/M}$ and relative weights $w_1$, $w_2$).

We also observe that the contrast sensitivity peak (maximum value) generally does not occur at one of the two extremes ratios ($w_1$=0 and $w_2$=1, or $w_1$=1 and $w_2$=0). It thus suggests that contrast sensitivity is maximized for some specific L-/M-cone excitation ratio $\alpha_{L/M}$, which varies from one observer to another.

The above-detailed technical solution can be implemented by using a digital display or by varying the chromaticity of at least two illuminating light sources while measuring the visual performance of the subject using a paper chart, e.g. a Pelli-Robson contrast sensitivity chart.

Moreover, instead of changing the chromaticity of the display or of the ambient illumination, the chromaticity of the visual stimulus can be also varied using chromatic filters worn by the subject.

The invention claimed is:

1. A method for selecting a color filter intended to be worn by a subject in order to improve his/her visual performance for a given visual task to be realized in a given environment, said method comprising the steps of:
submitting said subject to a colored spatio-temporal visual stimulus adapted to evaluate said visual performance for said given visual task, said visual stimulus being designed to differentially stimulate the M and L cones stimulation pathways of the eyes of the subject so that its chromaticity may be modified and take at least two distinct values, the visual stimulus being generated by a color display;
evaluating the visual performance of the subject based on his/her visual perception of said visual stimulus; and
selecting said color filter based on the results of said evaluation of the visual performance, the selected color filter improving the visual perception of said visual stimulus wherein the visual stimulus VS presented to the subject is of the form:

VS(x,y,t,λ)=C(λ)*L(x,y,t), where:

C(λ) is a spectral density of the visual stimulus; and

L(x,y,t) represents spatial and temporal luminance profiles of the visual stimulus, said visual stimulus being two monochromatic sinusoidal signals S(x,y,t) presented to the subject during a predetermined time and having a spatio-temporal pattern as a function of space (x,y) and time (t), the spatial and temporal luminance profiles of the visual stimulus are predetermined according to the subject's need for the given visual task, said subject's need is based on an improvement of the visual performance of the subject, the method further comprises a comparison step consisting in comparing at least one of said visual performance evaluation results with a predetermined reference value, the selection of said color filter being further based on the result of this comparison the spatial and temporal luminance profiles of the visual stimulus are predetermined according to the subject's need for the given visual task; and the predetermined reference value is a value of visual performance previously evaluated using said selection method, said the spatial and temporal luminance profile L(x,y,t) is proportional to [1+c*S(x,y,t)], wherein the signal S(x,y,t) is such that S(x,y,t)=cos(2*π*ω*t)*cos(2*π*x/∧$_x$)*cos(2*π*y/∧$_y$), where ω is the temporal pulsation ω, ∧$_x$ and ∧$_y$ are the periodicities of the signal S(x, y, t) along a vertical and an horizontal directions, c corresponding to a smallest contrast required to visually perceive a given signal S(x,y,t), the periodicities ∧$_x$ and ∧$_y$ and the temporal pulsation w defining the subject's need.

2. The method according to claim 1, wherein the visual stimulus is designed so that, while its chromaticity is modified during the submission step, its spatial and temporal luminance profiles are unchanged.

3. The method according to claim 1, wherein, at the step of selecting:

when the result of the comparison shows that the visual performance of the subject is improved, one chooses said color filter as having a spectral response n so that a spectral density CE(λ) of the environment surrounding the subject seen through said color filter is conformed to said spectral density C(λ) of the visual stimulus during the corresponding submission step; or when the result of the comparison shows that the visual performance of the subject is degraded, one chooses another color filter.

4. The method according to claim 3, wherein the color filter selected in the step of selecting depends on L-/M-cones excitation ratio depending on an activation ratio of the L cone and on an activation ratio of the M cone.

5. The method according to claim 3, wherein the step of selecting further depends on the spectral density of said given environment, said spectral density of said given environment depending on the spectral density of an illumination, a spectral reflection of the environment, and a chromatic filtering.

6. The method according to claim 1, wherein said spectral density C(λ) of the visual stimulus is such as C(λ)=w$_1$*C$_1$(λ)+w$_2$*C$_2$(λ), where:

C$_1$(λ) and C$_2$(λ) are different spectra designed to stimulate differently the L- or M-cones stimulation pathways of the eyes of the subject; and w$_1$ and w$_2$ are respective weights of said spectra, and where λ corresponds to the wavelength of said respective spectra.

7. The method according to claim 1, wherein the evaluated visual performance is one of the following:

spatial and/or temporal contrast sensitivity;

visual acuity;

chromatic sensitivity;

spectral sensitivity;

critical frequency fusion; and/or reading or driving ability.

8. The method according to claim 1, wherein, at evaluation step, the visual performance is evaluated by using a test chart illuminated by ambient light source, the spectral density of said ambient light source being modified during the submission step.

9. A system for selecting a color filter intended to be worn by a subject in order to improve his/her visual performance for a given visual task to be realized in a given environment, said system comprising:

display means configured to submit said subject to a colored spatio-temporal visual stimulus adapted to evaluate said visual performance for said given visual task, said visual stimulus being designed to differentially stimulate the M and L cones stimulation pathways of the eyes of the subject so that its chromaticity may be modified and take at least two distinct values, said system being arranged to:

evaluate the visual performance of the subject based on his/her visual perception of said visual stimulus displayed to the subject;

select said color filter based on the results of said evaluation of the visual performance, the selected color filter improving the visual performance of the subject wherein the visual stimulus VS presented to the subject is of the form: VX(x,y,t,λ)=C(λ)*L(x,y,t), where:

C(λ) is a spectral density of the visual stimulus; and

L(x,y,t) represents spatial and temporal luminance profiles of the visual stimulus, said visual stimulus being two monochromatic sinusoidal signals S(x,y,t) presented to the subject during a predetermined time and having a spatio-temporal pattern as a function of space (x,y) and time (t), the spatial and temporal luminance profiles of the visual stimulus are predetermined according to the subject's need for the given visual task, said subject's need is based on an improvement of the visual performance of the subject, said system being configured to compare at least one of said visual performance evaluation results with a predetermined reference value, the selection of said color filter being further based on the result of this comparison the spatial and temporal luminance profiles of the visual stimulus are predetermined according to the subject's need for the given visual task; and the predetermined reference value is a value of visual performance previously evaluated using said selection method, said the spatial and temporal luminance profile L(x,y,t) is proportional to [1+c*S(x,y,t)], wherein the signal S(x,y,t) is such that S(x,y,t)=cos(2*π*ω*t)*cos(2*π*x/∧$_x$)*cos(2*π*y/∧$_y$), where ω is the temporal pulsation ω, ∧$_x$ and ∧$_y$ are the periodicities of the signal S(x, y, t) along a vertical and an horizontal directions, c corresponding to a smallest contrast required to visually perceive a given signal S(x,y,t), the periodicities $\Lambda_x$ and $\Lambda_y$, and the temporal pulsation w defining the subject's need.

\* \* \* \* \*

UNITED STATES PATENT AND TRADEMARK OFFICE
CERTIFICATE OF CORRECTION

PATENT NO. : 12,004,810 B2
APPLICATION NO. : 16/769992
DATED : June 11, 2024
INVENTOR(S) : Zachary W. Wilkes It is certified that error appears in the above-identified patent and that said Letters Patent is hereby corrected as shown below:

In the Claims

Claim 1, Column 9, Line 28:
Delete "$\cos(2*\pi*\omega*t)*\cos(2*\pi*x/\wedge_x)*\cos(2*\pi*y/\wedge_y)$" and replace with
-- $\cos(2*\pi*\omega*t)*\cos(2*\pi*x/\wedge_x)*\cos(2*\pi*y/\wedge_y)$ --.

Claim 1, Column 9, Line 30:
Delete "$\wedge_x$ and $\wedge_y$" and replace with -- $\wedge_x$ and $\wedge_y$ --.

Claim 1, Column 9, Line 34:
Delete "$\wedge_x$ and $\wedge_y$" and replace with -- $\wedge_x$ and $\wedge_y$ --.

Claim 3, Column 9, Line 44:
Delete "spectral response n" and replace with -- spectral response $T\lambda$ --.

Claim 9, Column 10, Line 63:
Delete "$\cos(2*\pi*\omega*t)*\cos(2*\pi*x/\wedge_x)*\cos(2*\pi*y/\wedge_y)$" and replace with
-- $\cos(2*\pi*\omega*t)*\cos(2*\pi*x/\wedge_x)*\cos(2*\pi*y/\wedge_y)$ --.

Claim 9, Column 10, Line 65:
Delete "$\wedge_x$ and $\wedge_y$" and replace with -- $\Lambda_x$ and $\Lambda_y$ --.

Claim 9, Column 11, Line 2:
Delete "$\wedge_x$ and $\wedge_y$" and replace with -- $\Lambda_x$ and $\Lambda_y$ --.

Signed and Sealed this
Sixteenth Day of July, 2024

Katherine Kelly Vidal
*Director of the United States Patent and Trademark Office*